United States Patent [19]

Romine

[11] 4,234,542
[45] Nov. 18, 1980

[54] THIN COAT TEMPERATURE COMPENSATED RESISTANCE OXIDE GAS SENSOR

[75] Inventor: Donald J. Romine, Fostoria, Ohio

[73] Assignee: Bendix Autolite Corporation, Fostoria, Ohio

[21] Appl. No.: 7,134

[22] Filed: Jan. 29, 1979

[51] Int. Cl.³ ............................................. G01N 27/12
[52] U.S. Cl. ........................................ 422/98; 73/23; 338/34
[58] Field of Search .................................. 422/94–98; 338/34; 73/23, 27 R; 324/71 SN, 65 R, 65 P; 23/232 E

[56] References Cited

U.S. PATENT DOCUMENTS

| | | | |
|---|---|---|---|
| 3,901,067 | 8/1975 | Boardman, Jr. et al. | 338/34 X |
| 4,099,922 | 7/1978 | Yasuda et al. | 422/95 |
| 4,147,513 | 4/1979 | Bienkowski et al. | 422/98 X |
| 4,151,503 | 4/1979 | Cermak et al. | 73/27 R X |

FOREIGN PATENT DOCUMENTS 50-21795  3/1975  Japan ........................................ 422/98

Primary Examiner—Arnold Turk
Attorney, Agent, or Firm—William G. Kratz, Jr.; Raymond J. Eifler

[57] ABSTRACT

A temperature compensated resistive oxygen sensor and a method of manufacturing the same. On the surface of the sensor there are disposed in spaced relation three electrodes. One electrode and a portion of a second electrode is completely covered by a layer of a resistive material which is sensitive to changes in temperature. Another layer of resistive material which is sensitive to both changes in temperature and changes in the partial pressure of oxygen in the gas to which it is exposed covers the first resistive layer as well as the third electrode and the remaining portion of the second electrode. It is also a feature of the present invention that these layers are applied by shielding part of the surface of the sensor and applying the first layer by a hot thin-layer technique and by removing the shield and applying the second layer also by a hot thin-layer technique.

5 Claims, 3 Drawing Figures

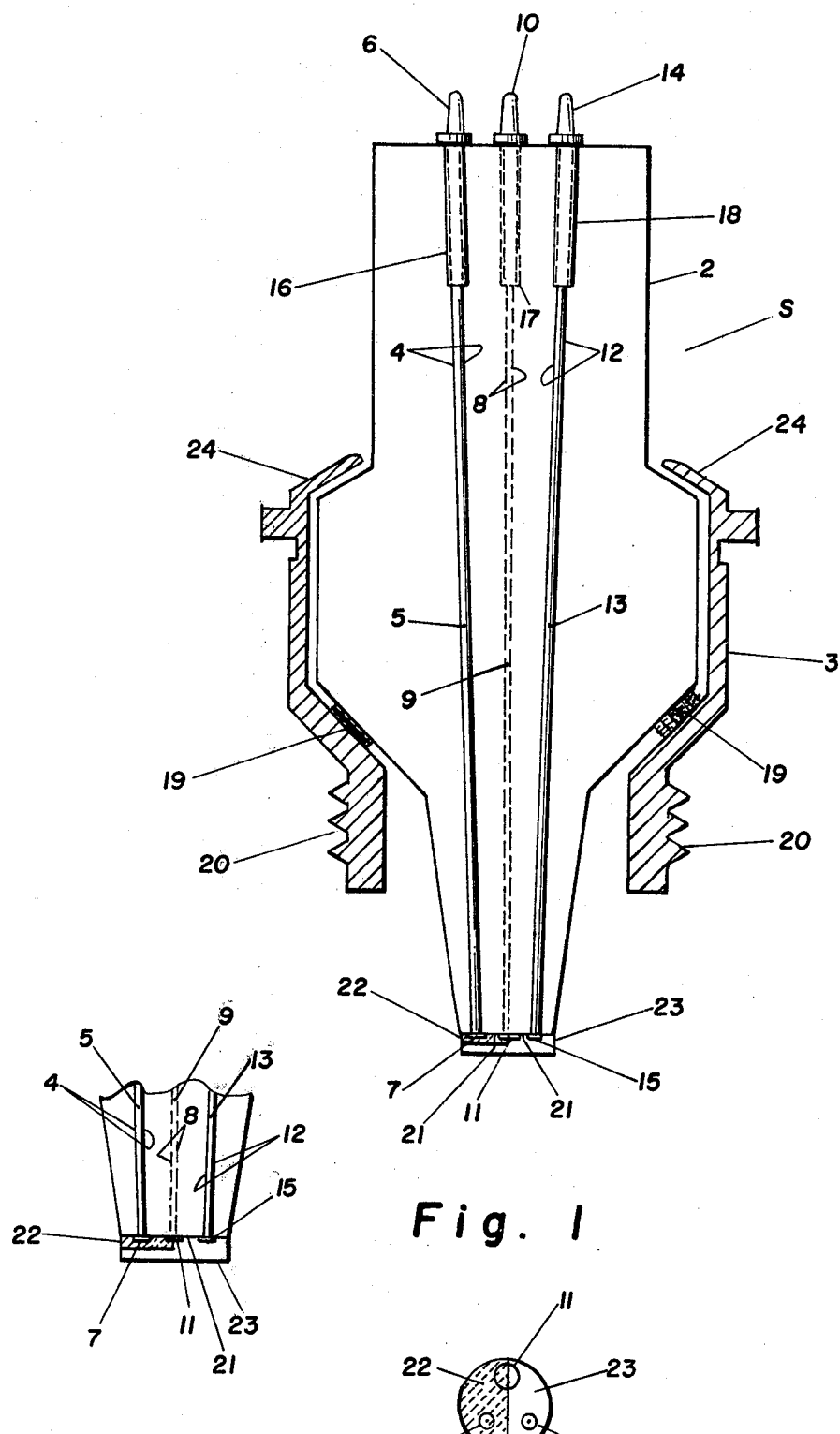
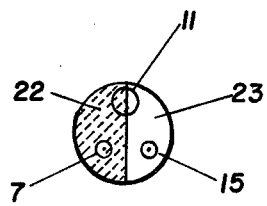
Fig. 1
Fig. 2
Fig. 3

THIN COAT TEMPERATURE COMPENSATED RESISTANCE OXIDE GAS SENSOR

BACKGROUND OF THE INVENTION

This invention is an apparatus for sensing the oxygen content in the exhaust gas of an automobile engine and a method of manufacturing such an apparatus. This invention is more particularly related to temperature compensated resistance type sensors.

The exhaust gas of automobile internal combustion engines contains several substances, including carbon monoxide, nitrogen oxides and various unoxidized or only partially oxidized hydrocarbons which contribute to air pollution. These substances can be converted to nonpoisons, like carbon dioxide, nitrogen and water by subjecting the exhaust gas to temperatures in excess of 600° C. while exposing it to catalysts, but, in order to achieve relatively complete conversion, it is necessary that the ratio of fuel to air that is provided to the engine be controlled so that it approximates stoichiometric proportions. Since it is known that the amount of oxygen contained in the exhaust gas provides an indication of whether such stoichiometric conditions exist, it has been suggested that an oxygen sensor be positioned in the exhaust system of an automobile so that it is exposed to its exhaust gas. This sensing element may be connected to a control device which regulates fuel supply and may thereby ensure that the correct ratio of fuel to air is provided to the engine so that the noxious components of the exhaust gas which are emitted into the atmosphere will be at as low a level as is possible.

Such oxygen sensing elements generally fall into two classes. The first of these classes includes solid electrolyte sensors. These sensors are made of a material such as zirconia which responds to the difference in the partial pressures of oxygen between one of its sides which is exposed to exhaust gas and another of its sides which is exposed to ambient air as a reference source. Such solid electrolyte sensors are described in greater detail in U.S. Pat. No. Re. 28,792, reissued April 27, 1976 (previously U.S. Pat. No. 3,400,054).

The other type of oxygen sensing element is generally referred to as a resistance type sensor. These sensors make use of an operative type material such as titania, the electrical resistance of which varies according to the amount of oxygen in the gas to which it is exposed. The principle and operation of such sensors are explained in U.S. Pat. No. 3,558,280 and the use of a titania resistance type sensor in an engine exhaust control is explained in U.S. Pat. No. 3,915,135.

While the resistance type sensors allow for simplicity of construction and installation by virtue of the fact that they do not have to be exposed to both the exhaust gas and a reference source of gas, a problem has been associated with their use. This problem results from the fact that although titania and similar materials are sensitive to changes in the oxygen partial pressure of the gas to which they are exposed, they are also sensitive to changes in temperature. For instance, a typical titania sensor must operate over a range from 300° C. to 900° C. but the electrical resistance of the sensor, over the entire range, does not change in a manner that permits a deliniation between a lean air to fuel mixture and a rich air to fuel mixture. Specifically, for a lean air to fuel mixture over the range of 300° C. and 900° C., the dc resistance of the typical titania sensor drops from $3 \times 10^9$ ohms down to about $2 \times 10^4$ ohms. While the dc resistance for a rich air to fuel mixture, over the same range, varies from $3 \times 10^6$ ohms down to about 40 ohms. Therefore, the resistance characteristics for a rich and a lean mixture for the sensor overlap. Accordingly, for any temperature excursion exceeding about 250° C. it is impossible, with an uncompensated titania sensor, to determine whether the air/fuel ratio is rich or lean. Of course, this is undesirable, as it would not be possible to control the air to fuel mixture.

A number of solutions have been suggested for this problem. It has, for example, been suggested that a heater element in conjunction with a thermostat be provided to maintain resistor type sensors at a constant temperature. Such heater arrangements, however, present certain disadvantages in that they are relatively complex and therefor are subject to failure and are expensive to manufacture. It has also been suggested that a resistor type sensor be made so that the sensor is, itself, temperature compensated. That is, a resistor type sensor is constructed with two resistors. In such a sensor there is provided a first resistor, the resistance of which varies as a function of temperature and the partial pressure of oxygen to which it is exposed, and a second resistor, the resistance of which varies only as a function of temperature. It is known that titania is a suitable material for the first resistor and that a stabilized zirconia material may be used in the second resistor. It is also known that such temperature compensated oxygen sensors may be employed in conjunction with certain circuitry which compares the voltages across the two resistors. This circuitry is thereby able to convert the temperature dependent input signal which it receives from the sensor to a temperature independent output signal by which it controls the air to fuel ratio provided to the engine.

Although such temperature compensated sensors are somewhat simpler than those sensors employing a heater and thermostat, their manufacture may still be unnecessarily complex. This complexity results from the fact that the component resistors of a form of these temperature compensated sensors are in the form of wafers or discs which are connected to electrical leads. If, for example, one of these wafers is composed of titania, titania must first be calcined, cooled, crushed, ball milled with water and then dried. The dry powder must then be blended with solvents, de-aired, cast into tape and dried. The wafers must then be punched from the tape and then suitably positioned on a support. Such a procedure is expensive and time consuming. Furthermore, it entails the risk that the resistor material will become contaminated and it exposes the persons performing it to the health and fire hazards associated with casting solvents.

It is, therefore, the object of the present invention to provide a temperature compensated oxygen sensor which avoids the above mentioned disadvantages of temperature compensated oxygen sensors currently available. Because the temperature compensated oxygen sensor of the present invention does not require the forming and emplacement of a sensor wafer, many of the steps previously associated with the manufacture of temperature compensated sensors are eliminated. Consequently, a durable and less costly sensor may be produced.

SUMMARY OF THE INVENTION

The present invention is a temperature compensated resistance type oxygen sensor in which the resistors are in the form of a layer or coating of resistive material which are connected to electrodes disposed on the surface of the sensor's insulating ceramic support which is to be exposed to exhaust gas. The present invention also provides a method by which a hot thin-layer technique, including plasma and flame spraying, may be employed to apply these resistive layers.

The first (7) of three electrodes (7, 11 and 15) is covered by a layer of a material (22), the resistance of which varies as a function only of temperature. The second electrode (11) is also covered, though only over a portion of its surface, by this material (22). A stabilized zirconium material may be used for this purpose. This temperature sensitive resistive layer is, in turn, covered by a temperature and oxygen sensitive resistive layer, that is, by a layer of a material (23) the resistance of which varies as a function of both temperature and the partial pressure of oxygen in the gas to which it is exposed. This temperature and oxygen sensitive resistive layer also covers the entire surface of the third electrode (15) and that portion of the second electrode (11) remaining uncovered by the temperature sensitive resistive layer. Titania may be used as the material of which the temperature and oxygen sensitive resistive layer is formed.

Another feature of the present invention is the method by which the above mentioned resistive layers are applied. After the electrodes have been emplaced on the surface of the ceramic exposed to the exhaust gas, a shield is placed over the part of the surface including the third electrode and part of the second electrode and zirconia or some other suitable temperature sensitive resistive material is applied to the exposed part of the surface of the ceramic support. Thereafter the shield is removed and titania and some other suitable temperature and oxygen sensitive material is applied to the entire surface also by a hot thin-layer technique.

BRIEF DESCRIPTION OF THE DRAWINGS

FIG. 1 is a cross sectional view of an oxygen sensor incorporating the principles of this invention;

FIG. 2 is a detailed view of a portion of the cross sectional view of the oxygen sensor shown in FIG. 1; and FIG. 3 is a plan view of the surface of the oxygen sensor which is exposed to exhaust gas.

DESCRIPTION OF THE PREFERRED EMBODIMENT

Referring to the drawings, the oxygen sensor S includes an insulating ceramic support 2 which is surrounded by a steel casing 3. Extending lengthwise through the ceramic support 2 are three passageways which allow three electrodes located on the side of the ceramic support which is exposed to the exhaust to be electrically connected to terminals on the opposite side of the ceramic support 2. The electrodes and the conductive leads are preferably formed of platinum, although the same may comprise other platinum group metals such as Ru, Rh, Pd or the like and their allows, or alloys of these platinum group metals and base metals, or the same may comprise gold, silver and the like metallic conductors. For the purpose of brevity, the invention will be described as having platinum electrodes, as well as leads, in the following description. While this connection may be accomplished by means of platinum wires, it is preferred that a platinum coating on the surface of these passageways be used to conduct current between said terminals and electrodes. Platinum coating 4 on the surface of passageway 5, for instance, allows current to flow between terminal 6 and electrode 7. In the same way, platinum coating 8 on the surface of 7. passageway 9 connects terminal 10 with electrode 11 and platinum coating 12 on the surface of passageway 13 connects terminal 14 with electrode 15. It is preferred that the diameter of electrode 11 be somewhat greater than electrodes 7 and 15. Additionally, the connection between platinum coatings 4, 8 and 12 and terminals 6, 10 and 14 is effected, respectively, by conductive seals 16, 17 and 18. Disposed between ceramic support 2 and steel casing 3 is a gasket 19. The steel casing 3 has a plurality of threads 20 which enable the sensor 3 to be attached to similar threads in the exhaust system of an automobile engine.

As has been noted, electrodes 7, 11 and 15 are disposed on the surface 21 of the ceramic support 2 which is to be exposed to the automobile engine's exhaust gas. Also disposed on that surface, in a particular arrangement, is a temperature sensitive resistive layer 22 and an oxygen and temperature sensitive resistive layer 23. The temperature sensitive resistive layer 22 is a layer of a material such as stabilized zirconia ($ZrO_2$), the resistance of which varies as a function only of temperature. The zirconia may be stabilized by elements such as calcium, barium, strontium, yttrium, lanthanum, scandium, ytterbium and samarium. Calcium stabilized zirconia and yttrium stabilized zirconia are well known and are obtained by adding approximately 0.05 to 0.3% (Mole weight) of yttria $Y_2O_3$ to zirconia ($ZrO_2$). Examples of materials that can be substituted for the zirconia are yttrium oxide ($Y_2O_3$), aluminum oxide ($Al_2O_3$), cerium oxide ($CeO_2$), hafnium ($HfO_2$) and thorium ($Th_2O_3$). Another important feature of the resistive layer 22 is that it is applied to surface 21 of the ceramic support 2 so that it completely covers the surface of electrode 7 and partially covers the surface of electrode 11.

The oxygen and temperature sensitive resistive layer 23 is comprised of a layer of a material, such as titania ($TiO_2$), that displays the property that its resistance is a function of both temperature and the partial pressure of oxygen in the gas to which it is exposed. While it is preferred that this layer be composed of titania, materials displaying similar properties, such as cobalt monoxide (CoO), may also be used. The oxygen and temperature sensitive resistive layer is applied so that it covers the entire surface of electrode 15 and that portion of the surface of electrode 11 remaining uncovered by the temperature sensitive resistive layer 22. The temperature and oxygen sensitive resistive layer 23 also covers the temperature sensitive resistive layer 22.

In the method by which the sensor of the present invention is manufactured, the three passageway ceramic support 2 is first extruded using standard spark plug insulator extrusion techniques. The passageways 5, 9 and 13 are then counterbored at the top of the support 2 so that they are of a sufficient diameter to receive terminals 6, 10 and 14. The ceramic support 2 is further formed using spark plug grinding techniques and is then fired in a kiln.

The platinum coatings 4, 8 and 12 may then be formed on the surfaces of passageways 5, 9 and 13 by pouring a platinum paste, the viscosity of which has been suitably adjusted, through said passageways. The platinum electrodes 7, 11 and 15 are thereafter formed so as to be conductively connected to platinum coatings 4, 8 and 12. After first being allowed to dry, the platinum coatings 4, 8 and 12 are fired at a temperature which is appropriate for the particular paste used.

At this point a part of the surface 21 of the ceramic support 2 is masked with a template or the like so that electrode 7 is exposed, electrode 11 is partially masked and electrode 15 is completely masked. A hot thin-layer technique, defined herein to include plasma spraying and flame spraying, is then used to apply to the unmasked part of surface 21 a fine grained powder of a ceramic oxide material, the resistance of which varies only as a function of temperature. A fine grained powder of zirconia is found to be suitable for this purpose. The temperature sensitive resistive layer 22, which covers the first electrode 7 and a portion of the second electrode 11, is thereby formed. The template is then removed and a fine grained powder of a ceramic oxide such as titania, the resistance of which varies as a function of temperature and the partial pressure of oxygen in the gas to which it is exposed, is applied to the entire surface 21. This material is also applied by a hot thin-layer technique so as to form the oxygen and temperature resistive layer 23. As has been noted, the temperature sensitive resistive layer 23 covers the entire surface 21 of the ceramic support 2, including the temperature sensitive layer 22, the third electrode 15 and that portion of the second electrode 11 not covered by the temperature sensitive resistive layer 22.

It is also found that enhanced results may be obtained if fine grained platinum powder is added to the ceramic oxide powder being plasma or flame sprayed. Such results are also obtained if the ceramic oxide powder is immersed in platinum chloride solution prior to plasma or flame spraying.

After the temperature sensitive resistive layer 22 and the oxygen and temperature sensitive resistive layer 23 are formed, the platinum coatings 4, 8 and 12 are then conductively connected to the metal terminals 6, 10 and 14, preferably by conductive seals 16, 17 and 18. Said seals may be formed by standard spark plug sealing techniques. That is, a copper-glass mixture which contains approximately forty percent copper is heated to the softening temperature of the glass and is applied to the passageways 5, 9 and 13. The terminals 6, 10 and 14 are then forced into the molten copper-glass mixture and maintained under pressure until the glass solidifies. The terminals may also be connected to the leads by other means such as with brazing compounds or metallic flake, or the like. The ceramic support 2 is then placed on gasket 19 within the steel casing 3. Finally, the steel casing 3 is crimped as at 24 and heat pressed in a known manner so as to seal the ceramic support 2 within the steel casing 3 and prevent the passage of gas.

There has been described a temperature compensated oxygen sensor for use in the exhaust path of an internal combustion engine which requires less processing and allows simpler assembly than do prior sensors. Because the sensor material is sprayed in place, the present invention eliminates the need to manufacture tapes or discs and thereby allows easier control of contamination, crystal size and porosity. Accordingly, a durable, accurate and less expensive sensor results.

I claim:

1. A temperature compensated electrochemical oxygen sensing element for determining the oxygen content in an exhaust gas of an internal combustion engine, comprising:
   (a) an insulating ceramic support having first, second and third electrodes disposed, in spaced relation to each other, on the surface of the ceramic support that is to be exposed to the exhaust gas;
   (b) a layer of a first resistance material, the resistance of which varies as a function only of temperature, said layer covering the first electrode and a portion of the second electrode; and
   (c) a layer of a second resistance material, the resistance of which varies as a function of temperature and the partial pressure of oxygen in the gas to which it is exposed, said layer covering the third electrode, the remaining portion of the second electrode and said layer of first resistance material.

2. The temperature compensated electrochemical oxygen sensing element defined in claim 1 wherein the first resistance material is a stabilized zirconia.

3. The temperature compensated electrochemical oxygen sensing element as defined in claim 1 wherein the second resistance material is selected from the group consisting of titanium dioxide and cobalt monoxide.

4. The temperature compensated electrochemical oxygen sensing element as recited in claim 1, including three terminals disposed on the end of the ceramic support opposite from the electrodes and where each of said terminals is electrically connected to a different electrode by electrical connecting means, said electrical connecting means being disposed inside three longitudinal passageways in the ceramic.

5. The temperature compensated electrochemical sensing element as defined in claim 4 where the electrical connecting means are platinum coatings on the interior surfaces of said passageways.

* * * * *